United States Patent
Panayi et al.

(10) Patent No.: US 9,137,993 B2
(45) Date of Patent: *Sep. 22, 2015

(54) HERBICIDAL PICOLINIC ACID SALT COMPOSITION

(71) Applicant: NUFARM AUSTRALIA LIMITED, Laverton North, Victoria (AU)

(72) Inventors: Aristos Panayi, Taylors Hill (AU); Chad Richard Ord Sayer, Brighton (AU)

(73) Assignee: NUFARM AUSTRALIA LIMITED, Laverton North, Victoria (AU)

( * ) Notice: Subject to any disclaimer, the term of this patent is extended or adjusted under 35 U.S.C. 154(b) by 0 days.

This patent is subject to a terminal disclaimer.

(21) Appl. No.: 14/499,677

(22) Filed: Sep. 29, 2014

(65) Prior Publication Data

US 2015/0031538 A1 Jan. 29, 2015

Related U.S. Application Data

(63) Continuation of application No. 13/703,509, filed as application No. PCT/AU2011/000730 on Jun. 17, 2011, now Pat. No. 8,865,625.

(60) Provisional application No. 61/356,911, filed on Jun. 21, 2010.

(51) Int. Cl.
| | |
|---|---|
| *A01N 57/00* | (2006.01) |
| *A01N 43/40* | (2006.01) |
| *A01N 37/10* | (2006.01) |
| *A01N 37/38* | (2006.01) |
| *A01N 37/40* | (2006.01) |
| *A01N 57/20* | (2006.01) |

(52) U.S. Cl.
CPC ............... *A01N 43/40* (2013.01); *A01N 37/10* (2013.01); *A01N 37/38* (2013.01); *A01N 37/40* (2013.01); *A01N 57/20* (2013.01)

(58) Field of Classification Search
None
See application file for complete search history.

(56) References Cited

U.S. PATENT DOCUMENTS

| | | | | |
|---|---|---|---|---|
| 3,317,549 | A * | 5/1967 | Johnston | 546/286 |
| 6,200,929 | B1 * | 3/2001 | Horibe et al. | 504/127 |
| 8,865,625 | B2 * | 10/2014 | Panayi et al. | 504/260 |
| 2011/0230349 | A1 * | 9/2011 | Buttimor | 504/244 |

FOREIGN PATENT DOCUMENTS

GB 1339315 * 12/1973

* cited by examiner

*Primary Examiner* — Alton Pryor

(57) ABSTRACT

A herbicidal concentrate composition comprising a mixture of the monomethylamine and dimethylamine salts of at least one picolinic acid herbicide of formula (Ia):

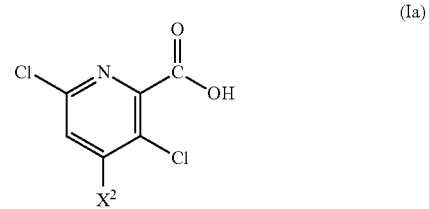

wherein $X^2$ is selected from hydrogen and amino.

15 Claims, No Drawings

HERBICIDAL PICOLINIC ACID SALT COMPOSITION

FIELD

The invention relates to a herbicidal composition of picolinic acid salts and in particular a composition of monomethylamine and dimethylamine salts of at least one picolinic acid of formula

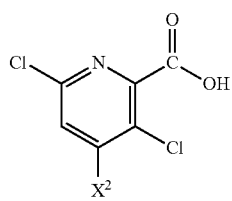

wherein $X^2$ is hydrogen or amino.

BACKGROUND

The picolinic acid class of herbicides comprise a substituted 2-pyridine carboxylic acid group and their ester and salt derivatives. The picolinic acid group of herbicides is used in control of perennial broad leaf weeds by pre emergent application to soil and post emergent foliar or soil application. They are useful in control of broadleaf weeds in grasses.

Examples of picolinic herbicidal compounds include compounds of formula (I)

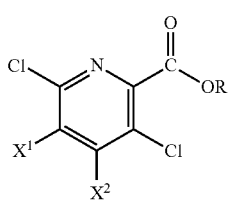

wherein
$X^1$ and $X^2$ are independently selected from hydrogen, chloro and amino; and
R is an ester or salt counter ion.

Specific examples of known picolinic acid herbicides include aminopyralid (4-amino-3,6-dichloropyridine-2-carboxylic acid) its esters and salts, picloram (4-amino-3,5,6-trichloropyridine-2-carboxylic acid also referred to as 4-amino-3,4,6-trichloropicolinic acid) its salts and esters and clopyralid (3,6-dichloropyridine-2-carboxylic acid also called 3,6-dichloropicolinic acid) its salts and esters.

The amine salts of the picolinic acid herbicides are in many cases water soluble and aqueous formulations of the amine salts are convenient to use. At the site of use the concentrate formulations can conveniently be diluted in a spray tank for soil or foliar application.

One of the significant limitations of amine salt compositions is their stability, particularly at high loadings. The poor solution stability is particularly a problem for low temperature storage of highly concentrated solutions, for example of at least 300 g/L and particularly at least 500 g/L (based on active acid equivalent). This places limitations on the storage and handling of the herbicidal picolinic acid amine salts with the result that the loading of salt needs to be lower than would normally be stable due to the propensity to form a significant proportion of crystalline deposits at low temperature which are not always readily redissolved.

The discussion of documents, acts, materials, devices, articles and the like is included in this specification solely for the purpose of providing a context for the present invention. It is not suggested or represented that any or all of these matters formed part of the prior art base or were common general knowledge in the field relevant to the present invention as it existed before the priority date of each claim of this application.

SUMMARY

We have found that the stability of certain picolinic acids in aqueous solution may be significantly improved allowing significantly higher loadings to be used by using a mixture of the monomethyl amine (MMA) and dimethylamine (DMA) salts of one or more picolinic acids.

Accordingly there is provided a herbicidal concentrate composition comprising a mixture of the monomethylamine and dimethylamine salts of at least one picolinic acid herbicide of formula (Ia)

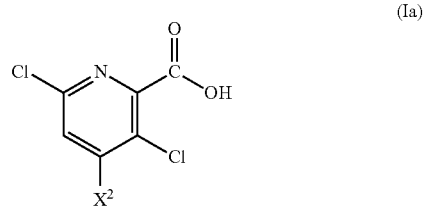

wherein $X^2$ is hydrogen or amino;

The mole ratio of monomethylamine to dimethylamine is, in one set of embodiments, in the range of from 5:95 to 95:5, preferably 10:90 to 90:10 and more preferably 20:80 to 80:20. In one set of embodiments the particularly preferred ratio is in the range of 70%-90% DMA to 30%-10% MMA. We found that this enhancement was not observed for picloram and was especially advantageous for clopyralid.

The picolinic acid component of the salts may be selected from the group consisting of aminopyralid and clopyralid and mixtures thereof.

The picolinic acid herbicide is preferably clopyralid, aminopyralid or mixture thereof.

The composition may comprise aminopyralid, clopyralid or mixture thereof in the form of one of the MMA salt and aminopyralid, clopyralid or mixture thereof in the form of the DMA salt. The composition in each form may be the same or different. In one set of embodiments the composition comprises clopyralid in each of the MMA and DMA salt forms. The picolinic acid may be aminopyralid or clopyralid and clopyralid is more preferred.

In an embodiment the concentration of picolinic acid herbicide of formula (Ia) in the form of the salts in the aqueous composition is at least 300 g/L (preferably at least 400 g/L, more preferably at least 500 g/L, more preferably at least 600 g/L still more preferably at least 625 g/L, still more preferably 650 g/L and still more preferably at least 700 g/L) based on herbicidal acid equivalent.

In one embodiment there is provided a solid composition for forming the aqueous liquid herbicide composition on dilution with water the solid composition comprising at least one of clopyralid and aminopyralid comprising a mixture of monomethylamine and dimethylamine salts and wherein the molar ratio of monomethylamine to dimethylamine is preferably from 5:95 to 95:5, more preferably 10:90 to 90:10 and still more preferably 20:80 to 80:20. In one set of embodiments the particularly preferred ratio is in the range of 70%-90% DMA to 30%-10% MMA.

In one embodiment the total MMA and DMA comprises at least 80% and more preferably from 80% to 130% by mole based on the number of mole of clopyralid and aminopyralid.

In another embodiment there is provided a process for preparing a composition described above comprising: providing at least one herbicidal picolinic acid of formula (I) (preferably clopyralid) and reacting the herbicide with methylamine and dimethylamine in a molar ratio of preferably 5:95 to 95:5, more preferably 10:90 to 90:10 and still more preferably 20:80 to 80:20 to provide a mixture of picolinic acid methylamine and dimethylamine salts. In one set of embodiments the particularly preferred ratio is in the range of 70%-90% DMA to 30%-10% MMA.

In another embodiment there is provided a method of preparing an aqueous liquid herbicide composition comprising dissolving monomethylamine salt of at least one of aminopyralid and clopyralid (preferably clopyralid) and dimethylamine salt of at least one of aminopyralid and clopyralid (preferably clopyralid) in an aqueous liquid to provide a composition as herein before described.

In one embodiment the above described concentrate further comprises a mixture comprising one or more other herbicides, including for example one or more herbicides selected from the group consisting of auxin herbicides such as MCPA and 24D; glycine herbicides such as glyphosate; and benzoic acid herbicides such asdicamba.

Throughout the description and the claims of this specification the word "comprise" and variations of the word, such as "comprising" and "comprises" is not intended to exclude other additives, components, integers or steps.

DETAILED DESCRIPTION

The composition comprises a mixture of MMA and DMA salts of at least one of aminopyralid and clopyralid herbicides with, in one set of embodiments, the molar ratio of MMA to DMA being in the range of from 5:95 to 95:5, preferably 10:90 to 90:10 and more preferably 20:80 to 80:20. In one set of embodiments the particularly preferred ratio is in the range of 70%-90% DMA to 30%-10% MMA.

The picolinic acid salt mixture is from a parent acid selected from compounds of formula (Ia)

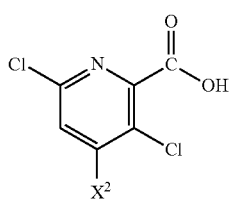

(Ia)

wherein
$X^2$ is selected from hydrogen and amino and mixtures of two or more thereof. Preferably the mixed salts are of clopyralid.

Specific examples of picolinic acid herbicides of formula (Ia) include aminopyralid (4-amino-3,6-dichloropyridine-2-carboxylic acid) and clopyralid (3,6-dichloropyridine-2-carboxylic acid also called 3,6-dichloropicolinic acid) and mixtures of two or more thereof.

While the composition may if desired include other herbicides including other amine salts of picolinic acid or auxin herbicide salts it is preferred that the monomethylamine and dimethylamine constitute at least 80% by weight of the amine content of the composition, preferably at least 90% by weight of the amine content and most preferably at least 95% by weight of the amine content.

Preferably the amine MMA and DMA will be present in a compound concentration in an amount of 80% to 130% by mole based on the total number of marks of clopyralid and aminopyralid.

Preferably the total of clopyralid and aminopyralid will constitute at least 70%, preferably at least 80% and more preferably at least 90% by mole of the total active herbicide content of the composition.

In a particularly preferred embodiment the concentration of herbicidal picolinic acid salt is at least 300 g/L (preferably at least 400 g/L, more preferably at least 500 g/L, more preferably at least 600 g/L, still more preferably 625 g/L, still more preferably 650 g/L and still more preferably at least 700 g/L) based on herbicidal acid equivalent.

The process for preparing the picolinic acid mixed salts may comprise providing at least one of clopyralid and aminopyralid (preferably clopyralid) and reacting the acids with monomethylamine and dimethylamine, preferably in a molar ratio of 5:95 to 95:5, more preferably 10:90 to 90:10 and still more preferably 20:80 to 80:20. In one set of embodiments the particularly preferred ratio is in the range of 70%-90% DMA to 30%-10% MMA, to provide a mixture of methylamine and dimethylamine salts of at least one of clopyralid and amino pyralid (preferably clopyralid).

Alternatively the process may comprise blending the salts, for example blending preformed solids, or dissolving a monomethylamine salt of at least one of aminopyralid and clopyralid and dimethylamine salt of at least one of aminopyralid and clopyralid in an aqueous liquid to provide a composition as hereinbefore described.

In one embodiment there is provided a method of controlling plant growth comprising diluting a concentrate composition comprising at least 300 g/L (preferably at least 400 g/L, more preferably at least 500 g/L, still more preferably at least 600 g/L, still more preferably 625 g/L, still more preferably 650 g/L and still more preferably at least 700 g/L) based on herbicidal acid equivalent of a mixture of MMA and DMA salts of at least one of clopyralid and aminopyralid (preferably clopyralid) with water and applying the diluted composition to plants or to soil in which growth of plants are to be controlled. The composition may, for example, be diluted with water to provide a concentration of clopyralid and aminopyralid (preferably solely clopyralid) herbicide salt in the range of from 0.01 g/L to 300 g/L (based on acid equivalent). The composition may be diluted for spray application to a concentration of 0.1 g/L to 150 g/L of for specific contact application using an applicator such as a rope or wick higher concentration of, for example 50 to 300 g/L may be desired.

The salt concentrate composition may, for example, depending on the picolinic acid salt mixture to be applied at a rate of from 0.01 kg/ha to 5 kg/ha based on total acid equivalent in order to achieve control of weeds.

In some cases solvents may be used in the concentrate picolinic acid salt compositions. Solvents such as ethylene glycol, may be used to further limit the formation of crystalline deposits during storage of the aqueous liquid concentrate. The compositions may, if desired, be free of non-aqueous solvents such as ethylene glycol. Accordingly in one embodiment the herbicide composition comprising a solution of salt of picolinic acid of formula (Ia) in the form of the monomethylamine salt and dimethylamine salt of picolinic acid of formula (Ia) wherein the molar ratio of monomethylamine to dimethylamine is preferably in the range of from 5:95 to 95:5, preferably 10:90 to 90:10 and more preferably 20:80 to 80:20 and may contain no more than 5% by weight non-aqueous solvents and more preferably is essentially free of non-aqueous solvents.

In one set of embodiments the particularly preferred ratio is in the range of 70%-90% DMA to 30%-10% MMA.

In a further embodiment the composition consists essentially of:

i) clopyralid salt herbicide in the form of the monomethylamine salt and clopyralid in the form of the dimethylamine salt wherein the molar ratio of monomethylamine to dimethylamine is preferably in the range of from 5:95 to 95:5, preferably 10:90 to 90:10 and more preferably 20:80 to 80:20. In one set of embodiments the particularly preferred ratio is in the range of 70%-90% DMA to 30%-10% MMA.

ii) water;

iii) no more than 10% by weight, preferably no more than 5% and more preferably no more than 2% by weight based on the total weight of the composition of additives selected from surfactants and compatibility agents; and iv) wherein the concentration of clopyralid salt herbicide in the aqueous composition is at least 300 g/L (preferably at least 400 g/L, more preferably at least 500 g/L, more preferably 600 g/L, more preferably at least 625 g/L, still more preferably 650 g/L and still more preferably at least 700 g/L) based on acid herbicidal acid equivalent.

The composition of the invention may and preferably will include a sequestriant/compatibility agent such as casein or EDTA which we have found to improve compatibility of the salts of picolinic acid of formula (Ia) and other herbicides. The amount of compatibility agent may be at least a compatibility enhancing amount. In a preferred embodiment the composition according to the invention further comprising casein in an amount of from 0.05 to 10 parts by weight casein per 100 parts by weight acid equivalent based on the picolinic acid of formula (Ia). The amount of casein is preferably from 0.01 to 5% by weight of a concentrate composition and more preferably is from 0.1 to 5% by weight of the composition.

The concentrate composition and or composition diluted with water may comprise one or more surfactants. Examples of surfactants include, nonaromatic-based surfactants, e.g. those based on heterocycles, olefins, aliphatics or cycloaliphatics, for example surface-active mono- or poly-alkyl-substituted and subsequently derivatized, e.g. alkoxylated, sulfated, sulfonated or phosphated, pyridine, pyrimidine, triazine, pyrole, pyrolidine, furan, thiophene, benzoxazole, benzthiazole and triazole compounds, and/or aromatic-based surfactants, e.g. mono- or poly-alkyl-substituted and subsequently derivatized, e.g. alkoxylated, sulfated, sulfonated or phosphated, benzenes or phenols. The surfactants are generally soluble in the solvent phase and are preferably suitable for emulsifying it (together with active ingredients dissolved therein) upon dilution with water to give a spray liquor. The surfactant component when present in compositions according to the invention can, for example, comprise nonaromatic or aromatic surfactants or mixtures of non-aromatic and aromatic surfactants.

The mixed salt picolinic acid herbicides of formula (Ia) (preferably clopyralid) with the preferred 5:95 to 95:5, preferably 10:90 to 90:10 and more preferably 20:80 to 80:20 molar ratio of MMA:DMA exhibit an enhanced cold storage stability and reduced crystal growth at cold temperatures. The compositions also exhibit an improvement in stability in solution when diluted with water of variable quality that tends to produce precipitation in other picolinic acid salts in concentrate compositions. In one set of embodiments the particularly preferred ratio is in the range of 70%-90% DMA to 30%-10% MMA.

The invention will now be described with reference to the following examples. It is to be understood that the examples are provided by way of illustration of the invention and that they are in no way limiting to the scope of the invention.

EXAMPLES

The following compositions were prepared and the composition stability tested on cold storage.

| Example | Formulation details | | | Comments |
|---|---|---|---|---|
| | 700 g/L Clopyralid (as MMA salt) | | | |
| Comparative Example 1 | Clopyralid tech 93% | 736.8 | g | Formulation is not stable. |
| | Monomethylamine(MMA) 40% | 287.1 | g | Crystallizes @ Room |
| | Water to | 1 | liter | Temperature. |
| | 650 g/L Clopyralid (as MMA salt) | | | |
| Comparative Example 2 | Clopyralid tech 93% | 684.2 | g | Formulation is not stable. |
| | MMA 40% | 266.6 | g | Crystallizes @ Room |
| | Water to | 1 | liter | Temperature. |
| | 600 g/L Clopyralid (as MMA salt) | | | |
| Comparative Example 3 | Clopyralid tech 93% | 631.6 | g | Formulation is not stable. |
| | MMA 40% | 246.1 | g | Crystallizes @ Room |
| | Water to | 1 | liter | Temperature. |
| | 550 g/L Clopyralid (as MMA salt) | | | |
| Comparative Example 4 | Clopyralid tech 93% | 579.0 | g | Formulation is not stable. |
| | MMA 40% | 225.6 | g | 100% Crystallization after 24 hrs |
| | Water to | 1 | liter | @ 0° C. |
| | 600 g/L Clopyralid (as TEA salt) | | | |
| Comparative Example 5 | Clopyralid tech 93% | 631.6 | g | Clopyralid acid does not solubilize |
| | Triethylamine TEA 85% | 576.0 | g | completely. Clopyralid-TEA salt is |
| | Water to | 1 | liter | not soluble at this concentration. |
| | 500 g/L Clopyralid (as TEA salt) | | | |

-continued

| Example | Formulation details | | Comments |
|---|---|---|---|
| Comparative Example 6 | Clopyralid tech 93% | 526.3 g | Clopyralid acid does not solubilize completely. Clopyralid-TEA salt is not soluble at this concentration. |
| | TEA 85% | 480.0 g | |
| | Water to | 1 liter | |
| | 400 g/L Clopyralid (as TEA salt) | | |
| Comparative Example 7 | Clopyralid tech 93% | 421.1 g | ~40% v/v crystallisation after 7 days @ 0° C. with seeding using crystals from the formulation. |
| | TEA 85% | 384.0 g | |
| | Water to | 1 liter | |
| | 700 g/L Clopyralid (as DMA salt) | | |
| Comparative Example 8 | Clopyralid tech 93% | 736.8 g | ~5% v/v crystallisation after 7 days @ 0° C. with seeding using crystals from the formulation. |
| | Dimethylamine DMA 60% | 287.1 g | |
| | Water to | 1 liter | |
| | 350 g/L Clopyralid (as TEA salt) | | |
| Comparative Example 9 | Clopyralid tech 93% | 368.4 g | ~2% v/v crystallisation after 5 days @ 0° C. with seeding using crystals from the formulation. |
| | TEA 85% | 336.0 g | |
| | Water to | 1 liter | |
| | 800 g/L Clopyralid (as DMA salt) | | |
| Comparative Example 10 | Clopyralid tech 93% | 842.1 g | ~10% v/v crystallisation after 5 days @ 0° C. with seeding using crystals from the formulation. |
| | DMA 60% | 328.1 g | |
| | Water to | 1 liter | |
| | 650 g/L Clopyralid (as DMA salt) | | |
| Comparative Example 11 | Clopyralid tech 93% | 684.2 g | ~15% v/v crystallisation after 2 days @ 0° C. with seeding using crystals from the formulation. |
| | DMA 60% | 266.6 g | |
| | Water to | 1 liter | |
| | 700 g/L Clopyralid (80% DMA: 20% MMA salt) | | |
| Example 1 | Clopyralid tech 93% | 736.8 g | No crystallisation @ 0° C. for 7 days with seeding using crystals from formulation. Passes Low Storage Stability (Collaborative International Pesticides Analytical Council—CIPAC MT39.3) |
| | DMA 60% | 229.7 g | |
| | MMA 40% | 57.4 g | |
| | Water to | 1 liter | |
| | 550 g/L Clopyralid (as DMA salt) | | |
| Comparative Example 13 | Clopyralid tech 93% | 579.0 g | ~5% v/v crystallisation after 1 day @ 0° C. with seeding using crystals from the formulation. |
| | DMA 60% | 225.6 g | |
| | Water to | 1 liter | |
| | 800 g/L Clopyralid (80% DMA: 20% MMA salt) | | |
| Example 2 | Clopyralid tech 93% | 842.1 g | ~1-2% v/v crystallisation after 24 hrs @ 0° C. without seeding. |
| | DMA 60% | 262.5 g | |
| | MMA 40% | 65.6 g | |
| | Water to | 1 liter | |
| | 750 g/L Clopyralid (80% DMA: 20% MMA salt) | | |
| Example 3 | Clopyralid tech 93% | 789.5 g | ~1-2% v/v crystallisation after 7 day @ 0° C. with seeding using crystals from the formulation. |
| | DMA 60% | 246.1 g | |
| | MMA 40% | 61.5 g | |
| | Water to | 1 liter | |
| | 750 g/L Clopyralid (70% DMA: 30% MMA salt) | | |
| Example 4 | Clopyralid tech 93% | 789.5 g | ~1% v/v crystallisation after 7 day @ 0° C. with seeding using crystals from the formulation. |
| | DMA 60% | 215.3 g | |
| | MMA 40% | 92.3 g | |
| | Water to | 1 liter | |
| | 725 g/L Clopyralid (80% DMA: 20% MMA salt) | | |
| Example 5 | Clopyralid tech 93% | 763.1 g | No crystallisation @ 0° C. for 7 days with seeding using crystals from formulation. Passes Low Storage Stability (CIPAC MT39.3) |
| | DMA 60% | 237.9 g | |
| | MMA 40% | 59.5 g | |
| | Water to | 1 liter | |
| | 725 g/L Clopyralid (90% DMA: 10% MMA salt) | | |
| Example 6 | Clopyralid tech 93% | 763.2 g | ~1% v/v crystallisation after 7 day @ 0° C. with seeding using |
| | DMA 60% | 267.6 g | |

-continued

| Example | Formulation details | | Comments |
|---|---|---|---|
| | MMA 40% | 29.7 g | crystals from the formulation. |
| | Water to | 1 liter | |
| | 725 g/L Clopyralid (70% DMA: 30% MMA salt) | | |
| Example 7 | Clopyralid tech 93% | 763.2 g | No crystallisation @ 0° C. for |
| | DMA 60% | 208.2 g | 7 days with seeding using crystals |
| | MMA 40% | 89.2 g | from formulation. |
| | Water to | 1 liter | Passes Low Storage Stability (CIPAC MT39.3) |

Comparative Examples 14 to 21

These comparative Examples examine the stability of picloram (a picolinic acid not of formula Ia) compositions containing a mixture of DMA and MMA salts.

| Comparative Example No. | Formulation details | Amount (g) | Comments |
|---|---|---|---|
| | 2,4-D 600 g/L + Picloram 150 g/L (90% DMA: 10% MMA) | | |
| 14 | Picloram acid technical (93%) | 161.3 | The formulation is not stable. |
| | 2,4-D acid technical (97%) | 618.6 | Approx. 30% crystallization |
| | MMA (40%) | 26.3 | when the formulation if left |
| | DMA (60%) | 236.4 | to stand @ Room temperature |
| | water | to 1 L | (R.T) for 24 hrs. |
| | 2,4-D 600 g/L + Picloram 150 g/L (60% DMA: 40% MMA) | | |
| 15 | Picloram acid technical (93%) | 161.3 | The formulation is not stable. |
| | 2,4-D acid technical (97%) | 618.6 | Approx. 10% crystallization |
| | MMA (40%) | 105.1 | when the formulation if left |
| | DMA (60%) | 157.6 | to stand @ R.T for 24 hrs. |
| | water | to 1 L | |
| | 2,4-D 600 g/L + Picloram 150 g/L (100% DMA) | | |
| 16 | Picloram acid technical (93%) | 161.3 | The actives are not fully |
| | 2,4-D acid technical (97%) | 618.6 | soluble. A large amount of |
| | DMA (60%) | 262.7 | active material remains |
| | water | to 1 L | unreacted/undissolved. |
| | 2,4-D 600 g/L + Picloram 150 g/L (70% DMA: 30% MMA) | | |
| 17 | Picloram acid technical (93%) | 161.3 | The formulation is not stable. |
| | 2,4-D acid technical (97%) | 618.6 | Approx. 80% crystallisation |
| | MMA (40%) | 78.8 | when the formulation if left |
| | DMA (60%) | 183.9 | to stand @ R.T for 24 hrs. |
| | water | to 1 L | |
| | 2,4-D 600 g/L + Picloram 150 g/L (100% MMA) | | |
| 18 | Picloram acid technical (93%) | 161.3 | The actives are not fully |
| | 2,4-D acid technical (97%) | 618.6 | soluble. A large amount of |
| | MMA (40%) | 262.7 | active material remains |
| | water | to 1 L | unreacted/undissolved. |
| | 2,4-D 600 g/L + Picloram 150 g/L (20% DMA: 80% MMA) | | |
| 19 | Picloram acid technical (93%) | 161.3 | The actives are not fully |
| | 2,4-D acid technical (97%) | 618.6 | soluble. A large amount |
| | MMA (40%) | 210.2 | of active material remains |
| | DMA (60%) | 52.5 | unreacted/undissolved. |
| | water | to 1 L | |
| | 2,4-D 600 g/L + Picloram 150 g/L (40% DMA: 60% MMA) | | |
| 20 | Picloram acid technical (93%) | 161.3 | The actives are not fully |
| | 2,4-D acid technical (97%) | 618.6 | soluble. A large amount |
| | MMA (40%) | 157.6 | of active material remains |
| | DMA (60%) | 105.1 | unreacted/undissolved. |

-continued

| Comparative Example No. | Formulation details | Amount (g) | Comments |
|---|---|---|---|
| | water | to 1 L | |
| | 2,4-D 600 g/L + Picloram 150 g/L (50% DMA: 50% MMA) | | |
| 21 | Picloram acid technical (93%) | 161.3 | The actives are not fully soluble. A large amount of active material remains unreacted/undissolved. |
| | 2,4-D acid technical (97%) | 618.6 | |
| | MMA (40%) | 131.4 | |
| | DMA (60%) | 131.4 | |
| | water | to 1 L | |

The picloram MMA/DMA salts were found to have poor stability in comparison with the corresponding clopyralid salt mixtures.

The invention claimed is:

1. A herbicidal concentrate composition comprising a mixture of the monomethylamine and dimethylamine salts of clopyralid, wherein the mixture of clopyralid salts is present in aqueous solution at a concentration of at least 300 g/L, based on herbicidal acid equivalent and the mole ratio of dimethylamine (DMA) to monomethylamine (MMA) is in the range of from 70%-90% DMA to 30%-10% MMA; wherein the herbicidal concentrate composition comprising the DMA salt of clopyralid and the MMA salt of clopyralid has enhanced stability and reduced crystal growth at cold temperatures compared to an equivalent herbicidal concentrate where the DMA salt of clopyralid is present while the MMA salt of clopyralid is absent or the MMA salt of clopyralid is present while the DMA salt of clopyralid is absent.

2. A herbicidal composition according to claim 1, wherein the mixture of clopyralid salts is present in aqueous solution in a concentration of at least 400 g/L, based on herbicidal acid equivalent.

3. The herbicidal composition according to claim 1, wherein the composition further comprises one or more other herbicides.

4. A herbicidal composition according to claim 1, wherein the composition further comprises one or more other herbicides selected from the group consisting of other auxin herbicides and glycine herbicides.

5. A herbicidal composition according to claim 1, wherein the composition comprises one or more additional herbicides selected from the group consisting of MCPA, 2,4-D, dicamba and glyphosate.

6. A herbicidal composition according to claim 1, wherein the composition further comprises MCPA.

7. A herbicidal composition according to claim 1, wherein the composition further comprises dicamba.

8. A herbicidal composition according to claim 1, wherein the composition further comprises 2,4-D.

9. A herbicidal composition according to claim 1, wherein the composition further comprises glyphosate.

10. A composition according to claim 1, wherein the composition comprises casein in an amount of from 0.01% to 5% by weight of the composition.

11. A process for preparing a composition in any one of the previous claims comprising providing a herbicide comprising clopyralid acid and reacting the clopyralid acid with methylamine and dimethylamine in a molar ratio of in the range of 70%-90% DMA to 30%-10% MMA wherein the concentration of clopyralid is at least 300 g/L based on herbicidal acid equivalent.

12. A process according to claim 11, wherein the herbicide further comprises an additional herbicide.

13. A process according to claim 12, wherein the additional herbicide is selected from auxin herbicides and glycine herbicides.

14. A process according to claim 12, wherein the additional herbicide is selected from the group consisting of MCPA, 2,4-D and dicamba.

15. A process according to claim 12, wherein the additional herbicide is glyphosate.

* * * * *